(12) United States Patent
Song et al.

(10) Patent No.: US 12,430,755 B2
(45) Date of Patent: Sep. 30, 2025

(54) DATA PROCESSING METHOD

(71) Applicant: MEDIT CORP., Seoul (KR)

(72) Inventors: Myoung Woo Song, Seoul (KR); Ki Nam Ko, Seoul (KR); Dong Hwa Kang, Seoul (KR)

(73) Assignee: MEDIT CORP., Seoul (KR)

( * ) Notice: Subject to any disclaimer, the term of this patent is extended or adjusted under 35 U.S.C. 154(b) by 483 days.

(21) Appl. No.: 17/826,183

(22) Filed: May 27, 2022

(65) Prior Publication Data

US 2022/0392066 A1    Dec. 8, 2022

(30) Foreign Application Priority Data

Jun. 3, 2021    (KR) .................. 10-2021-0072280
Apr. 12, 2022   (KR) .................. 10-2022-0045050

(51) Int. Cl.
*G06V 30/14*    (2022.01)
*G06T 7/00*     (2017.01)

(52) U.S. Cl.
CPC .. *G06T 7/0012* (2013.01); *G06T 2207/20021* (2013.01); *G06T 2207/30036* (2013.01)

(58) Field of Classification Search
CPC ........ G06V 10/30; G06V 10/22; G06V 10/26; G06F 16/9577; A61B 6/032; A61B 5/02028; G16H 50/30; G16H 30/40; G06T 7/62
See application file for complete search history.

(56) References Cited

U.S. PATENT DOCUMENTS

2018/0028063 A1    2/2018   Elbaz
2019/0269485 A1*   9/2019   Elbaz .................. A61B 1/00016

FOREIGN PATENT DOCUMENTS

| EP | 3689218 A1 | 8/2020 |
| JP | 2012-165333 A1 | 8/2012 |
| KR | 10-2018-0121494 A1 | 11/2018 |
| KR | 10-2022432 B1 | 9/2019 |
| KR | 10-2020-0099997 A1 | 8/2020 |
| WO | 2020/185019 A1 | 9/2020 |

OTHER PUBLICATIONS

Non-final Office Action mailed Apr. 17, 2024 from the Korean Patent Office for Korean Application No. 10-2022-0045050.
Extended European Search Report mailed Oct. 20, 2022 for European Application No. 22176599.3.

* cited by examiner

*Primary Examiner* — Phuoc H Doan
(74) *Attorney, Agent, or Firm* — Insight Law Group, PLLC; Seung Lee

(57) ABSTRACT

Provided is a data processing method according to the present disclosure including: a scan data acquiring operation of acquiring scan data expressing an object, a reliability determining operation of determining a reliability of at least one evaluation area including at least one unit area for evaluating the scan data, and an indicating operation of indicating the evaluation area as a predetermined mark depending on the reliability of the evaluation area.

17 Claims, 14 Drawing Sheets

DATA PROCESSING METHOD

CROSS-REFERENCE TO RELATED APPLICATIONS

The present application claims priority from and benefit of Korean Patent Application Nos. 10-2021-0072280 filed on Jun. 3, 2021, and 10-2022-0045050 filed on Apr. 12, 2022, the disclosures of which are incorporated by reference herein in their entirety.

TECHNICAL FIELD

The present disclosure relates to a data processing method, and more specifically, to a data processing method of acquiring a three-dimensional scan data expressing an object, and determining reliability of the scan data, thereby improving the completeness of the scan data.

BACKGROUND ART

A three-dimensional scanning technology is being used in the fields of various industries such as measurement, inspection, reverse engineering, content generation, CAD/CAM for dental treatment, and medical device, and its practicality is further expanding due to the improvement of scanning performance caused by the development of a computing technology. In particular, in the dental treatment field, since the three-dimensional scanning technology is performed for patient treatment, a three-dimensional model acquired through the three-dimensional scanning is required to have high precision.

In the process of generating the three-dimensional model through a three-dimensional scanner, the three-dimensional scanner acquires the entire three-dimensional model data by converting the image data (two-dimensional or three-dimensional) acquired by capturing an object to be measured into the three-dimensional model. In addition, the more closely the object to be measured is captured, the more images the three-dimensional scanner acquires, and thus, the reliability of the final data for the three-dimensional model converted in real time is improved.

A series of exemplary procedures for conventional orthodontic treatment of patients are described to emphasize the necessity for highly reliable data acquisition. For the orthodontic treatment of patients, a user acquires scan data expressing the patient's oral cavity. At this time, aligned three-dimensional scan data is acquired by scanning a maxilla, a mandible, and an occlusal state therebetween of the patient. The acquired scan data is transmitted to a factory and used for producing an orthodontic treatment product. However, when an accurate orthodontic treatment product may not be manufactured because there is a cavity in a part of the scan data (e.g., between the teeth) in the factory, the user should additionally scan the patient's oral cavity again, which requires an additional visit of the patient, resulting in discomfort to the patient. In addition, when the orthodontic treatment product is produced by arbitrarily filling the cavity of the scan data in the factory, distortion of the scan data may occur, and there is a possibility that an inaccurate orthodontic treatment product may be produced.

Accordingly, recently, the research and development, in which the three-dimensional scanning is performed and then the user checks the scanning results to induce an additional scanning for the low-reliability part, thereby increasing the precision and reliability of the final data for the object to be measured and improving the user convenience, are being actively conducted.

Conventionally, the precision and/or reliability of the final data for the object to be measured depended on a user's personal determination. However, there is a problem in that it is difficult to trust the precision of the final data because the criterion of the user's personal determination is ambiguous and the determination depends only on his/her sense.

In order to improve such a situation, recently, a method of visually displaying reliability by giving a predetermined color or applying a pattern to a three-dimensional model has been used. For example, depending on the reliability of the data configuring the three-dimensional model, there is a user interface (UI) in which the low-reliability area is displayed in red, the medium-reliability area is displayed in yellow, and the high-reliability area is displayed in green.

However, the method of visually displaying reliability by applying the color or pattern to the three-dimensional model as described above may be inefficient when the supplementation for a part of the three-dimensional model is required. Exemplarily, when a part between an arbitrary first tooth and an arbitrary second tooth is not closely scanned, the corresponding portion may be displayed in red. However, when the remaining portions other than the corresponding portion have high reliability and are displayed in green as a whole, it may be difficult for the user to visually check the location and/or direction of the low-reliability area displayed in red.

Accordingly, a method for supplementing scan data by more easily identifying a portion in which supplementation is required on a three-dimensional model is being studied.

RELATED ART DOCUMENT

Patent Document (Patent Document) Korean Patent No. 10-2022432 (registered on Sep. 18, 2019)

SUMMARY OF INVENTION

Technical Problem

An object of the present disclosure is to provide a data processing method, which may indicate a portion having low reliability among scan data in a predetermined mark so that a user may easily check the portion with the low reliability, so that the user may quickly, additionally scan the corresponding portion of an object to supplement the scan data.

Objects of the present disclosure are not limited to the above-mentioned objects, and other objects not mentioned will be clearly understood by those skilled in the art from the following descriptions.

Solution to Problem

In order to achieve the above-described object, there is provided a data processing method according to the present disclosure including: a scan data acquiring operation of acquiring scan data expressing an object, a reliability determining operation of determining a reliability of at least one evaluation area including at least one unit area for evaluating the scan data, and an indicating operation of indicating the evaluation area as a predetermined mark depending on the reliability of the evaluation area.

In addition, the data processing method according to the present disclosure may further include other additional operations, including the above-described operations, so that the user may easily check the completeness of the scan data, and the user may additionally scan a portion of the object corresponding to the evaluation area having low reliability, thereby improving the reliability of the scan data.

Advantageous Effects of Invention

The user can easily acquire the scan data having the sufficient reliability using the data processing method according to the present disclosure.

In addition, by determining the reliability for each evaluation area using the data processing method according to the present disclosure, the user can easily check the portion on which the low-reliability portion is concentrated, and supplement the portion of the scan data in which supplementation is quickly required through the additional scan.

In addition, by variously setting the shape of the mark indicating the evaluation area depending on the low degree of reliability, it is possible to emphasize the evaluation area having lower reliability, and the user can sufficiently supplement and scan the portion of the scan data in which supplementation is a lot required, thereby improving the reliability of the scan data 300.

In addition, the mark overlaid by the scan data can be changed as the overlaid mark, thereby easily checking the location of the evaluation area in which supplementation is required, which exists on the rear surface of the scan data even without interfering with checking the shape of the scan data.

In addition, by allowing the mark indicating the evaluation area with reliability improved by the supplementation scan data acquired in the supplementation scan operation to be removed in real time, the user can easily check the supplemented state of the scan data.

DESCRIPTION OF EMBODIMENTS

Figure 1:
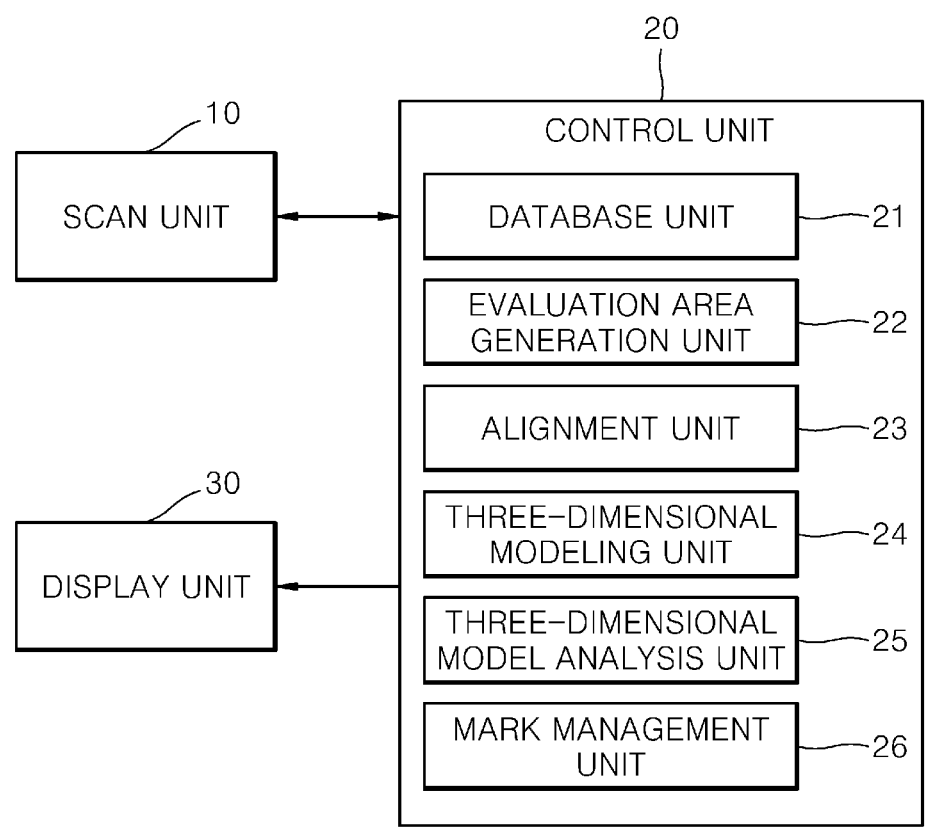
FIG. 1 is a flowchart of a data processing device in which a data processing method according to the present disclosure is performed.

Hereinafter, some embodiments of the present disclosure will be described in detail with reference to exemplary drawings. In adding reference numerals to the components of each drawing, it should be noted that the same components are given the same reference numerals as much as possible even when they are indicated in different drawings. In addition, in describing the embodiment of the present disclosure, when it is determined that a detailed description of a related known configuration or function interferes with the understanding of the embodiment of the present disclosure, the detailed description thereof will be omitted.

In describing the components according to the embodiment of the present disclosure, terms such as first, second, A, B, (a), (b), etc. may be used. These terms are only for distinguishing the components from another, and the essence, order, or sequence of the corresponding components are not limited by the terms. In addition, unless otherwise defined, all terms used herein, including technical or scientific terms, have the same meaning as commonly understood by those skilled in the art to which the present disclosure pertains. Terms such as those defined in a commonly used dictionary should be interpreted as having a meaning consistent with the meaning in the context of the related art, and should not be interpreted in an ideal or excessively formal meaning unless explicitly defined in the present application.

FIG. 1 is a flowchart of a data processing device 1 in which a data processing method according to the present disclosure is performed.

The data processing device 1 performed in the data processing method according to the present disclosure will be described with reference to FIG. 1. The data processing device 1 includes a scan unit 10, a control unit 20, and a display unit 30. The scan unit 10 may scan an object to acquire scan data expressing the object. The scan unit 10 scans the object to acquire image data expressing the object (the image data may include at least one of two-dimensional image data and three-dimensional image data). To acquire a three-dimensional model of the object, the scan unit 10 may be a three-dimensional scanner capable of three-dimensional scanning of the object. For example, the scan unit 10 may be a handheld scanner in which a user may grip and scan an object at various scan distances and scan angles. As another example, the scan unit 10 may be a table-type scanner that mounts the object on a tray and rotates and tilts the object with respect to a camera to scan the object.

Meanwhile, the object scanned by the scan unit 10 may include at least one of shape information of an oral cavity and color information of the oral cavity. Exemplarily, the object may be an inside of a patient's actual oral cavity. As another example, the object may be an oral model made of plaster modeled after the patient's oral cavity. As another example, the object may be an impression model that is a mold of the oral cavity model.

Data acquired by the scan unit 10 scanning the object may be transmitted to the control unit 20 capable of data communication with the scan unit 10. The control unit 20 may be a device equipped with a microprocessor capable of data transmission/reception and data operation. For example, the control unit 20 may be at least one of various known operation devices including a desktop PC, a tablet PC, and a server.

The control unit 20 may include a database unit 21. The database unit 21 may store data received from the scan unit 10. In addition, the database unit 21 may store at least one logic necessary for operating other components of the control unit 20. For example, the database unit 21 may store alignment logic for mutually aligning the plurality of image data acquired by the scan unit 10. As another example, the database unit 21 may store three-dimensional modeling logic for modeling the aligned data as scan data that is a three-dimensional model. As still another example, the database unit 21 may analyze the reliability of the scan data for each evaluation area to store reliability evaluation logic for generating a mark indicating an evaluation area having low reliability and thresholds for reliability evaluation.

In addition, the control unit 20 may include an evaluation area generation unit 22. The evaluation area generation unit 22 may generate at least one evaluation area in a three-dimensional space. For example, after the scan data is acquired, the evaluation area generation unit 22 may generate at least one evaluation area to correspond to the size of the scan data. At this time, the evaluation area may include at least one unit area. As another example, before the scan data is acquired, the evaluation area generation unit 22 may be previously partitioned and generated with a constant volume in a three-dimensional space. The evaluation area generated by the evaluation area generation unit 22 may be used to evaluate the reliability of at least a part of the scan data, and a predetermined mark may be generated to inform a user of the low reliability of at least a part of the evaluation area. A process of evaluating the reliability of the evaluation area to generate a mark and indicating the evaluation area will be described later.

In addition, the control unit 20 may include an alignment unit 23. The alignment unit 23 may align the image data acquired by the scan unit 10. The alignment unit 23 may use a known alignment method to align the image data. For example, the alignment unit 23 may align the image data using an iterative closest point (ICP) method, but the alignment method of the alignment unit 23 is not necessarily limited to the disclosed example.

In addition, the control unit 20 may include a three-dimensional modeling unit 24. The three-dimensional modeling unit 24 may model the aligned image data as scan data having a three-dimensional shape. The scan data may three-dimensionally express the object on a user interface screen. The scan data generated by the three-dimensional modeling unit 24 may be moved in parallel and rotated within a three-dimensional space, as necessary.

In addition, the control unit 20 may include a three-dimensional model analysis unit 25. The three-dimensional model analysis unit 25 may analyze the reliability of the evaluation area including at least a part of the scan data. The three-dimensional model analysis unit 25 may determine the reliability of the evaluation area, and the reliability of the evaluation area may be determined by a ratio of the unit area satisfying a predetermined condition within the evaluation area. For example, when the number of three-dimensional points included in the unit area is the number of threshold points or more, it may be determined that the predetermined condition is satisfied. As another example, when a scan angle range of the three-dimensional point included in the unit area is a threshold scan angle range or more, it may be determined that the predetermined condition is satisfied.

In addition, the control unit 20 may include a mark management unit 26. Based on the reliability of the evaluation area determined by the three-dimensional model analysis unit 25, the mark management unit 26 may generate the mark for indicating the evaluation area having low reliability to control the mark to indicate the evaluation area. At this time, a shape of the mark generated by the mark management unit 26 may be different depending on the reliability of the indicated evaluation area. In addition, the mark management unit 26 may determine that the mark is overlaid by the scan data. When it is determined that the mark is overlaid by the scan data, the mark management unit 26 may change the corresponding mark to the overlaid mark. Meanwhile, when it is determined that the overlaid mark is not overlaid by the scan data, the mark management unit 26 may change the corresponding overlaid mark to a general mark.

The display unit 30 may display at least a part of a control process of the control unit 20. For example, the display unit 30 may display at least one of a process of aligning real-time images of the object acquired by the scan unit 10 and the image data acquired by the scan unit 10, a process of generating the scan data that is a three-dimensional model, a process of determining reliability of the scan data for each evaluation area to allow the mark to indicate a specific portion, and a process of changing the general mark to the overlaid mark depending on whether the mark is overlaid by the scan data. However, what the display unit 30 displays is not limited to the examples listed above. As the display unit 30, a known visual display device may be used. For example, the display unit 30 may be at least one of a visual display device including a monitor, a tablet screen, and a projection screen.

The data processing method according to the present disclosure may be performed by the data processing device 1 as described above, and data processing processes according to the data processing method may be implemented by an operation of each of the components of the data processing device 1 and the interaction between the components.

Hereinafter, the data processing method according to the present disclosure will be described in detail.

Figure 2:
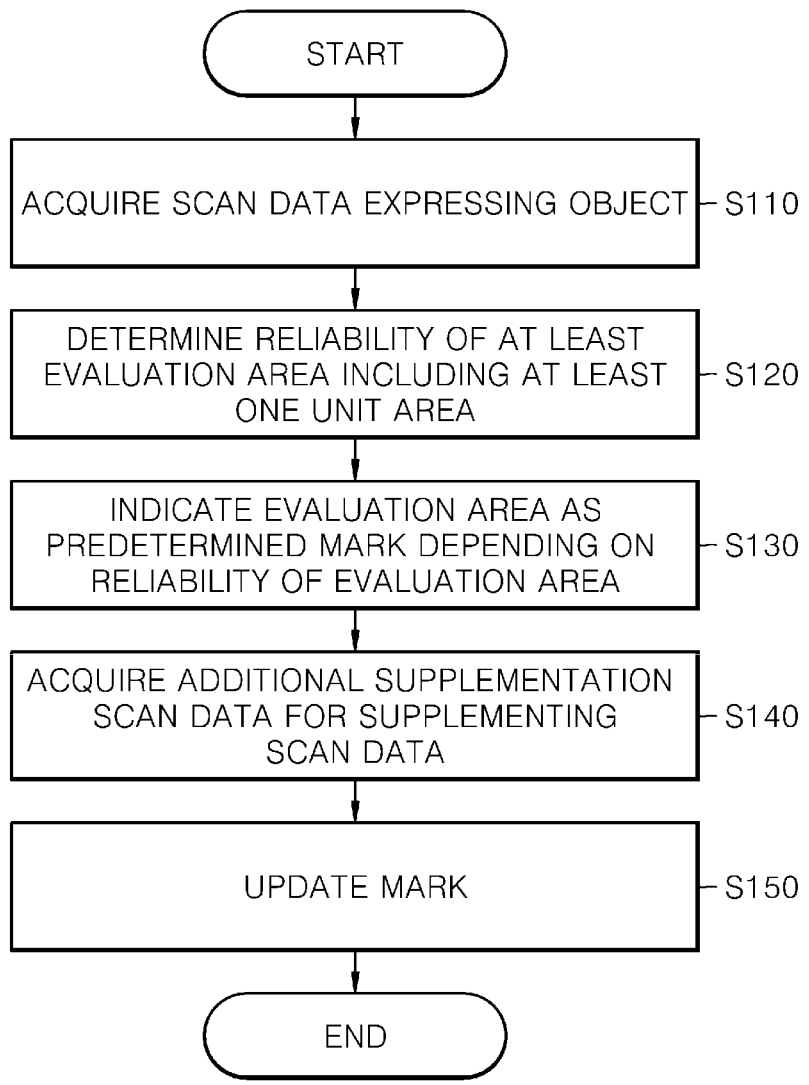
FIG. 2 is a schematic flowchart of the data processing method according to the present disclosure.

FIG. 2 is a schematic flowchart of the data processing method according to the present disclosure.

Referring to FIG. 2, the data processing method according to the present disclosure may include a scan data acquiring operation (S110), a reliability determining operation (S120), an indicating operation (S130), and a supplementation scanning operation (S140).

Hereinafter, each operation of the data processing method according to the present disclosure will be described in detail.

The data processing method according to the present disclosure may include the scan data acquiring operation (S110). A scan unit may acquire the image data that is the basis of the scan data by scanning the object. The scan unit may acquire a plurality of image data to transmit the image data to a control unit capable of communicating with the scan unit. The scan unit and the control unit may be connected by wire or wirelessly. The control unit may generate and acquire the scan data expressing the object by three-dimensional-modeling the image data transmitted by the scan unit. Meanwhile, the scan data may include at least one three-dimensional point. For example, the scan data may be generated by a set of three-dimensional points. In the reliability determining operation (S120) to be described later, the reliability of the evaluation area may be determined based on the three-dimensional points configuring the scan data. The process of determining the reliability of the evaluation area in the reliability determining operation (S120) will be described later.

Hereinafter, one exemplary process for generating the evaluation area used to determine a part of the scan data in which supplementation is required will be described.

Figure 3:
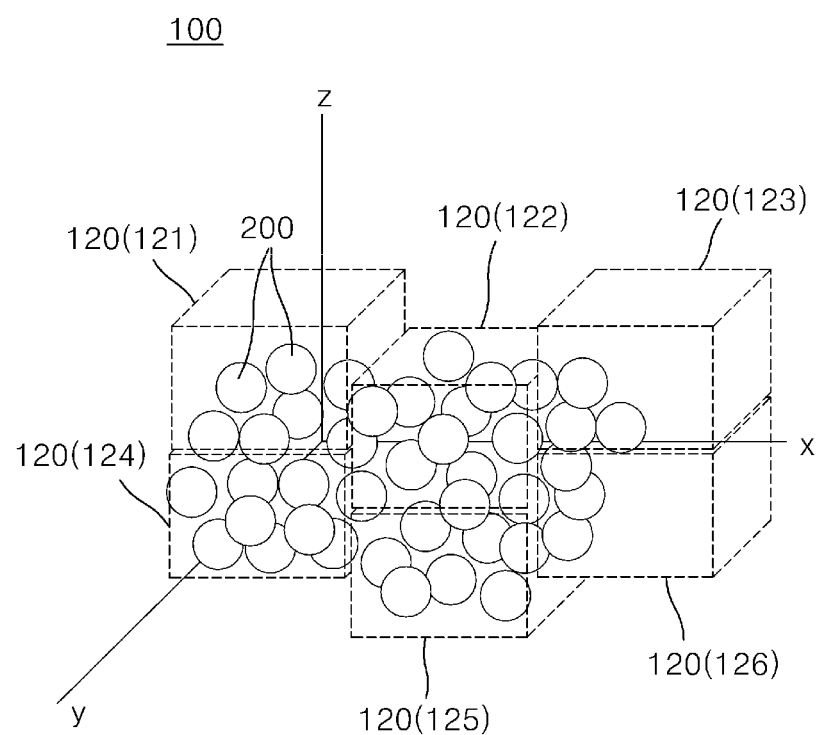
FIG. 3 shows a process of generating an evaluation area within a three-dimensional space in the data processing method according to one embodiment of the present disclosure.

FIG. 3 shows a process of generating an evaluation area within a three-dimensional space in the data processing method according to one embodiment of the present disclosure.

Referring to FIG. 3, after the scan data acquiring operation (S110) is performed to acquire the scan data, an evaluation area 120 may be partitioned and generated in a three-dimensional space 100 to correspond to the scan data. In other words, the evaluation area generating operation in which the at least one evaluation area 120 is generated may be performed after the scan data acquiring operation (S110).

As shown in FIG. 3, a plurality of three-dimensional points 200 configuring the scan data may be acquired and arranged on the three-dimensional space 100. The evaluation area generation unit of the control unit may generate the evaluation areas 120 according to the arranged shapes of the three-dimensional points 200 corresponding to the scan data. For example, the evaluation areas 120 may include a first evaluation area 121, a second evaluation area 122, a third evaluation area 123, a fourth evaluation area 124, a fifth evaluation area 125, and a sixth evaluation area 126. However, the above-described number of evaluation areas 120 is merely illustrative, and an appropriate number of evaluation areas 120 may be used to quickly and accurately determine the portion of the scan data in which supplementation is required.

Meanwhile, the volumes of the evaluation areas 120 may be increased or decreased, as necessary. When the volumes of the evaluation areas 120 are set to be relatively large, a point indicated by a mark to be described later may be different from the portion of the scan data in which supplementation is required. When the volumes of the evaluation areas 120 are set to be relatively small, an excessively large number of marks may be generated in some cases, resulting in user confusion by the generated and displayed marks. Accordingly, the evaluation areas 120 should be set to have an appropriate volume.

Hereinafter, another exemplary process in which the evaluation area used to determine the portion of the scan data in which supplementation is required is generated will be described.

Figure 4:
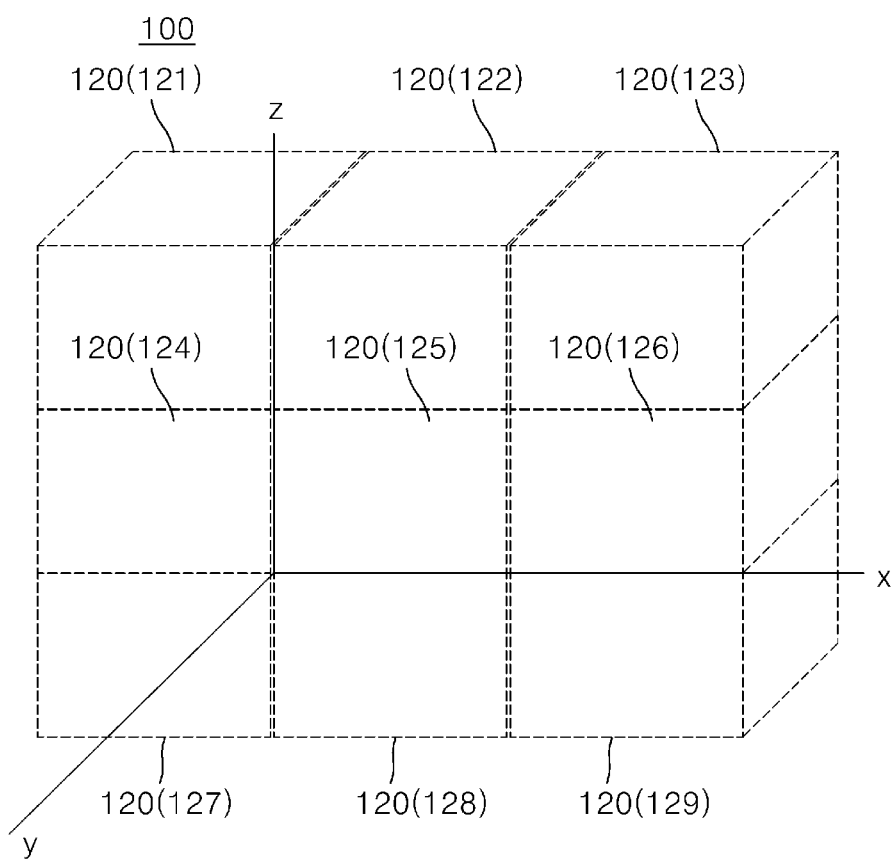
FIG. 4 shows a process of previously partitioning and generating an evaluation area within a three-dimensional space according to a data processing method according to another embodiment of the present disclosure.
Figure 5:
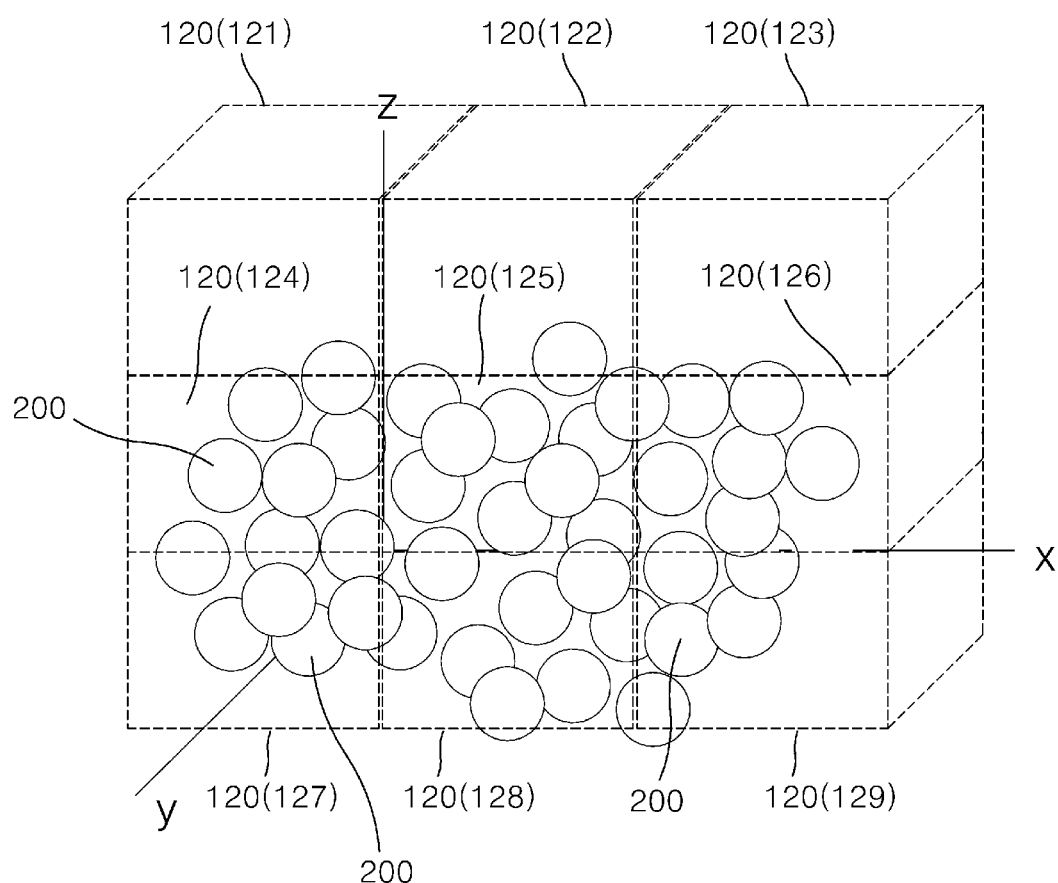
FIG. 5 shows a process of acquiring a three-dimensional point of scan data within the evaluation area in the data processing method according to another embodiment of the present disclosure.

FIG. 4 shows a process of previously partitioning and generating the evaluation area 120 within the three-dimensional space 100 in a data processing method according to another embodiment of the present disclosure, and FIG. 5 shows a process of acquiring the three-dimensional point 200 of the scan data within the evaluation area 120 in the data processing method according to another embodiment of the present disclosure.

Referring to FIGS. 4 and 5, the evaluation area 120 may be previously partitioned and generated in the three-dimensional space 100 before the scan data is acquired. In other words, the evaluation area generating operation may also be performed before the scan data acquiring operation (S110).

As shown in FIG. 4, the evaluation area generation unit of the control unit may partition the three-dimensional space 100 to generate a plurality of evaluation areas 120 before the scan data is acquired. For example, the evaluation area generation unit previously partitions the three-dimensional space 100 to generate a first evaluation area 121, a second evaluation area 122, a third evaluation area 123, a fourth evaluation area 124, a fifth evaluation area 125, a sixth evaluation area 126, a seventh evaluation area 127, an eighth evaluation area 128, and a ninth evaluation area 129. For example, the total occupation space occupied by the evaluation areas 120 may be formed to correspond to the size of the scan data or to be larger than the size of the scan data.

Meanwhile, since the scan data is acquired to design the orthodontic treatment product to be applied to the patient's teeth or treat the patient's teeth, the evaluation area 120 may be formed to the size capable of covering the tooth area or the tooth area and a part of a gum area adjacent to the tooth area among the scan data.

At least one evaluation area 120 may include at least one unit area. The unit area may be a minimum unit area configuring a three-dimensional space. For example, the unit area may have a form of voxel data having a predetermined volume. The unit area may include curvature information and/or color information of the corresponding portion of the scan data. In addition, the unit area may have at least one three-dimensional point, and each three-dimensional point may have scan angle information acquired by the three-dimensional point.

Hereinafter, the reliability determining operation (S120) will be described.

Figure 6:
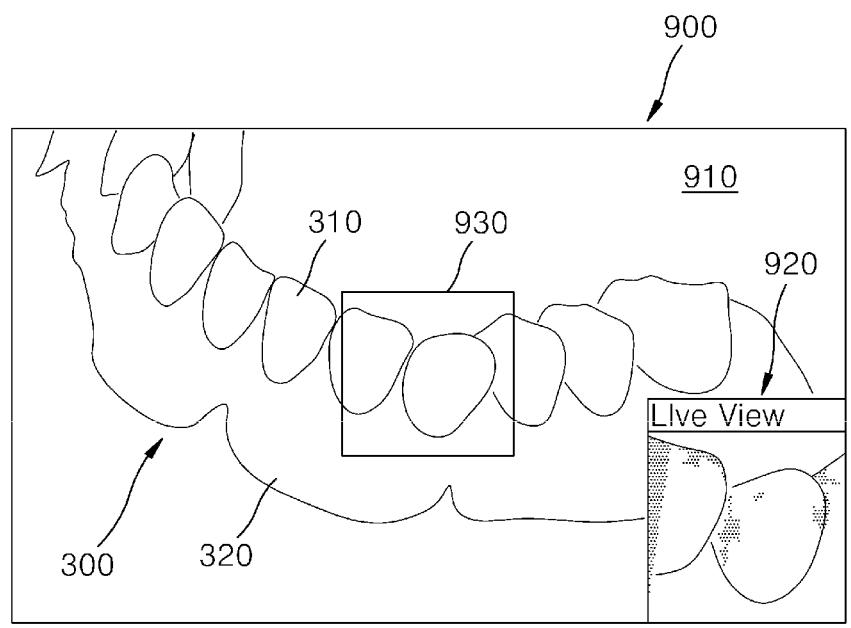
FIG. 6 shows a process of acquiring the scan data from a user interface screen in the data processing method according to the present disclosure.
Figure 7:
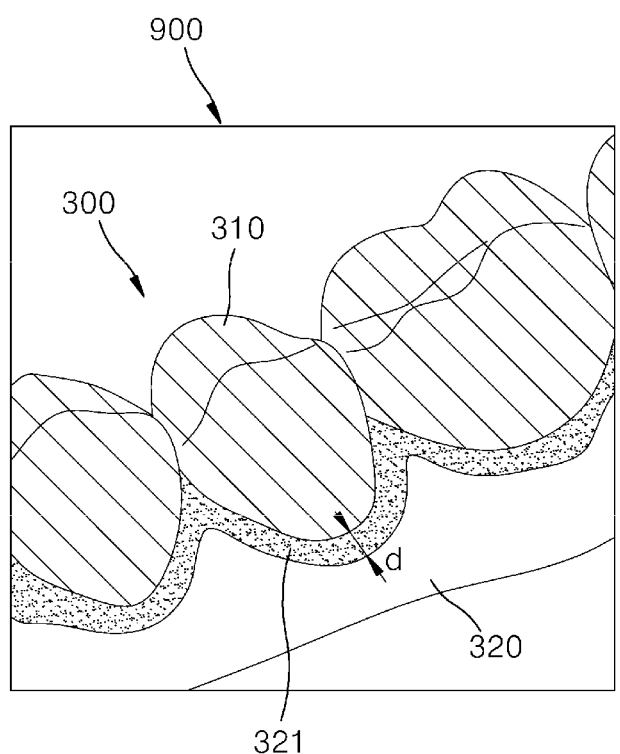
FIG. 7 shows an object on which a reliability determination operation is performed.
Figure 8:
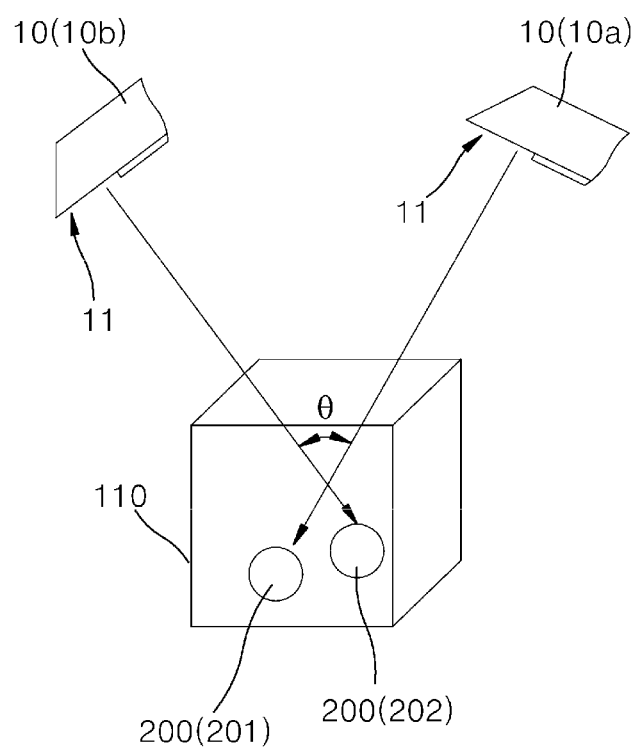
FIG. 8 shows a process of measuring a scan angle range of the 3D point in an arbitrary unit area included in the evaluation area.

FIG. 6 shows a process of acquiring the scan data 300 on a user interface screen 900 in the data processing method according to the present disclosure, and FIG. 7 shows an object on which the reliability determining operation (S120) is performed. In addition, FIG. 8 shows a process of measuring a scan angle range θ of the three-dimensional point 200 in the arbitrary unit area 110 included in the evaluation area 120.

Referring to FIGS. 2 and 6 to 8, the data processing method according to the present disclosure may include the reliability determining operation (S120). In the reliability determining operation (S120), the three-dimensional model analysis unit of the control unit may determine the reliability of at least one evaluation area 120 for evaluating the scan data 300. Meanwhile, the reliability of the evaluation area 120 for evaluating the scan data may be determined by the ratio of the unit area 110 satisfying the predetermined condition in the evaluation area 120. At this time, in order to determine the reliability of the evaluation area 120, a plurality of unit areas may be included in the evaluation area.

First, referring to FIG. 6, the scan unit may scan the object to acquire the scan data 300. The acquired scan data 300 may be displayed in real time on a workspace area 910 of the user interface screen 900. Meanwhile, a real-time image display area 920 may display a two-dimensional image of the object scanned by the scan unit on one side of the user interface screen 900 in real time. A scan box 930 displayed in a polygonal shape on the workspace area 910 may express a location of the scan data 300 corresponding to a location of the object currently being scanned by the scan unit.

The scan data 300 may include a tooth area 310 expressing the object's teeth and a gum area 320 including the object's gum. The scan data 300 should express the precise shape of the object's teeth in the tooth area 310. In other words, the tooth area 310 of the scan data 300 should have high reliability. Accordingly, the reliability determining operation (S120) may be performed with respect to at least a part of the tooth area 310.

In addition, in order to design the orthodontic treatment product for patient treatment, curvature information of the gum areas adjacent to some teeth may be required. Accordingly, as necessary, the reliability determining operation (S120) is performed with respect to the tooth area 310 and also performed with respect to an adjacent gum area 321 that is at least a part of the gum area 320 adjacent to the tooth area 310 within a predetermined interval d. By determining the portion of the scan data 300 in which supplementation is required, including the adjacent gum area 321, the user may acquire the scan data 300 with high completeness capable of providing a precise orthodontic treatment product to the patient.

Meanwhile, before the scan data acquiring operation (S110), the user may select a tooth and type of an object to be treated. For example, when a crown type is selected by setting a second tooth as a target tooth, the reliability determining operation (S120) may be performed only for the evaluation area 120 including the tooth area corresponding to first and third teeth that are teeth adjacent to the second tooth, and 30th and 31th teeth that are antagonist teeth, or 31th and 32nd teeth. As another example, when an inlay type is selected by setting the second tooth as the target tooth, the reliability determining operation (S120) may be performed only on the evaluation area 120 including the tooth area corresponding to the second tooth.

In the reliability determining operation (S120), the reliability of the evaluation area 120 is determined by the ratio of the unit area 110 satisfying the predetermined condition among the plurality of unit areas 110 included in the corresponding evaluation area 120. For example, when the evaluation area 120 includes 10 unit areas 110 and there are 8 unit areas 110 satisfying the predetermined condition among them, the reliability of the corresponding evaluation area 120 may be determined as 80%, which is the ratio of the number of unit areas satisfying the predetermined condition to the number of total unit areas. When the reliability of the evaluation area 120 is a preset threshold reliability or more, the corresponding evaluation area 120 may be determined as a high-reliability evaluation area. Conversely, when the reliability of the evaluation area 120 is smaller than the preset threshold reliability, the corresponding evaluation area 120 may be determined as a low-reliability evaluation area. The scan data 300 having the low-reliability evaluation area 120 may not accurately express the object, and there is a risk of providing inaccurate treatment to the patient. In order to prevent such a risk, it is necessary to induce the user to visually and easily check the low-reliability evaluation area 120.

Meanwhile, the predetermined condition to be satisfied by the unit area 110 may include a condition for the number of three-dimensional points. For example, the unit area 110 may have a form of voxel data, and the reliability of the evaluation area 120 may be determined by comparing the number of three-dimensional points 200 of the voxel data with the number of threshold points. For example, as the scan data 300 is acquired, the unit area 110 may have at least one three-dimensional point therein. As the number of three-dimensional points of the unit area 110 increases, the reliability of the portion of the scan data 300 corresponding to the unit area 110 may increase. For example, when the number of three-dimensional points of the unit area 110 is 5 or more, it may be determined that the corresponding unit area 110 satisfies the above condition, and the unit area 110 has sufficient reliability. On the other hand, when the number of three-dimensional points of the unit area 110 is smaller than the number of threshold points, it may be determined that the unit area 110 does not satisfy the above condition.

As another example, the predetermined condition to be satisfied by the unit area 110 may include a condition of the scan angle range of the three-dimensional point. For example, the unit area 110 may have a form of voxel data, and the reliability of the evaluation area 120 may be determined by comparing the scan angle range of the three-dimensional point 200 of the voxel data and the threshold scan angle range. As shown in FIG. 8, the scan unit 10 may scan the same portion of the object to have different scan angles. A scan unit 10a at a first location may acquire a first three-dimensional point 201 within the unit area 110, and a scan unit 10b at a second location may acquire a second three-dimensional point 202 within the unit area 110. The first three-dimensional point 201 and the second three-dimensional point 202 may each have a scan angle acquired by the incidence of the light reflected from the surface of the object through an opening 11. For example, the scan angle may refer to a direction of a normal vector of each of the three-dimensional points 200. The scan angle range $\theta$ may be acquired through a difference between the scan angle of the first three-dimensional point 201 and the scan angle of the second three-dimensional point 202. More specifically, the scan angle range $\theta$ may refer to an angle between the normal vector of the first three-dimensional point 201 and the normal vector of the second three-dimensional point 202. In other words, the scan angle range $\theta$ may be acquired by the dot product of the normal vector of the first three-dimensional point 201 and the normal vector of the second three-dimensional point 202.

Meanwhile, even when the same portion of the object is scanned, the reliability of the scan data 300 acquired by scanning the object in a relatively wide angle range may be higher than the reliability of the scan data 300 acquired by scanning the object in a relatively narrow angle range. Accordingly, when the scan angle range $\theta$ between the three-dimensional points 200 of the unit area 110 is the threshold scan angle range (e.g., 30°) or more, it may be determined that the corresponding unit area 110 satisfies the above condition, and it may be determined that the corresponding unit area 110 has sufficient reliability. On the other hand, when the scan angle range $\theta$ of the three-dimensional point 200 of the unit area 110 is smaller than the threshold scan angle range, it may be determined that the corresponding unit area 110 does not satisfy the above condition.

When the unit area 110 includes three or more three-dimensional points 200, the scan angle range $\theta$ may be determined as the largest angle range of the angle ranges formed by two three-dimensional points 200 among the plurality of three-dimensional points 200. Accordingly, the reliability of the portion of the scan data 300 corresponding to the unit area 110 having the large scan angle range $\theta$ may increase.

Hereinafter, the indicating operation (S130), which is one operation of the data processing method according to the present disclosure, will be described.

Figure 9:
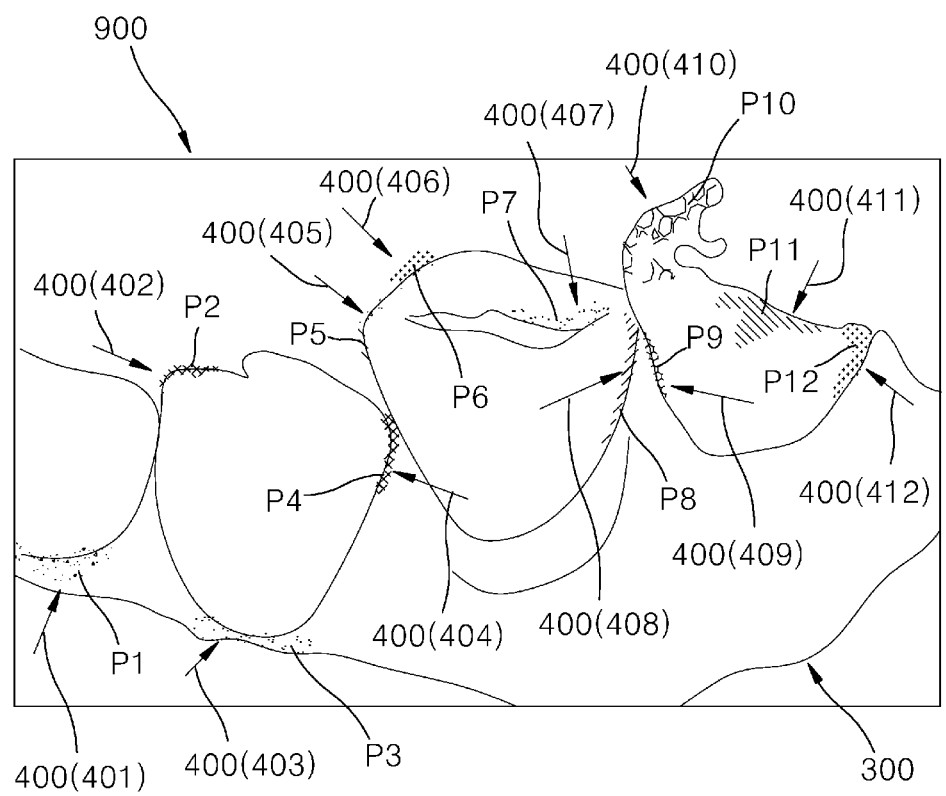
FIG. 9 shows a state in which the reliability determination operation is performed and a predetermined mark is indicated on the scan data.

FIG. 9 shows a state in which the reliability determining operation (S120) is performed and a predetermined mark 400 is indicated on the scan data 300.

Referring to FIGS. 2 and 9, the data processing method according to the present disclosure may include the indicating operation (S130). In the indicating operation (S130), the mark management unit of the control unit may determine, generate, and manage the shape of the mark to indicate the evaluation area 120 as a predetermined mark depending on the reliability of the evaluation area 120.

As shown in FIG. 9, the scan data 300 may be displayed on the user interface screen 900, and the marks 400 with an arrow shape may be displayed on the scan data 300 depending on the reliability of the evaluation area 120 determined for each evaluation area 120.

For example, the portion of the scan data 300 in which supplementation is required among the scan data 300 may be displayed through a predetermined pattern. For example, for the scan data 300, the portion of the scan data 300 in which supplementation is required may be represented by the reliability of the evaluation area 120 determined according to the above-described reliability determining operation (S120) through a first pattern to a 12th pattern p1, p2, p3, p4, p5, p6, p7, p8, p9, p10, p11, p12. As another example, the above-described patterns p1, p2, p3, p4, p5, p6, p7, p8, p9, p10, p11, p12 may not be displayed on the portion of the scan data 300 in which supplementation is required among the scan data 300, and only the mark 400 with the arrow shape may indicate the portion of the scan data 300 in which supplementation is required among the scan data 300.

In addition, the indicating operation (S130) may display the plurality of marks 400 for indicating the pattern. For example, the indicating operation (S130) may display a first mark to a 12th mark 401, 402, 403, 404, 405, 406, 407, 408, 409, 410, 411, 412 corresponding to the first pattern to the 12nd pattern p1, p2, p3, p4, p5, p6, p7, p8, p9, p10, p11, p12.

The shape of the mark 400 may include a three-dimensional arrow directed to the center of the evaluation area 120. In other words, through the mark 400 with the arrow shape directed to the center of the low-reliability evaluation area 120, the user may easily identify the portion of the scan data 300 in which supplementation is required. Compared to the conventional method of expressing the highs and lows of the reliability on the surface of the scan data 300 through a predetermined color, the present disclosure has advantages in that the location of the low-reliability evaluation area 120 may be accurately indicated through the mark 400, and the user may easily check the portion of the scan data 300 in which supplementation is required to quickly supplement the above portion.

Meanwhile, the shape of the mark 400 may also be expressed in other shapes other than the arrow shape. For example, the mark 400 may be expressed in the form of a predetermined color (e.g., red) indicating the entire evaluation area 120. As another example, the mark 400 may be expressed in the form of an emphasis line emphasizing a rim of the evaluation area 120.

In addition, a direction of the mark 400 may be parallel to a direction of an average normal vector of the three-dimensional points 200 included in the evaluation area 120. As described above, by allowing the direction of the mark 400 to be set to be parallel to the direction of the average normal vector of the three-dimensional points 200, and the mark 400 to be directed to the center of the evaluation area 120 (i.e., allowing an extension of the mark 400 to pass through the center of the evaluation area 120), the mark 400 may indicate the accurate location and direction of the scan data 300 to be supplemented, and the user may check the mark 400 to easily supplement the scan data 300.

Meanwhile, since the marks 400 indicate the low-reliability evaluation area 120, the user may accurately supplement only the portion of the scan data 300 in which supplementation is required, thereby quickly improving the overall reliability of the scan data 300.

As another example, the mark 400 may have a different shape depending on the reliability of the evaluation area 120. In other words, depending on the reliability of the low-reliability evaluation area 120, the necessity of supplementing the specific low-reliability evaluation area 120 may be emphasized. For example, when the reliability of the arbitrary first low-reliability evaluation area 120 is 20% and the reliability of the arbitrary second low-reliability evaluation area 120 is 40%, a thickness of the mark 400 indicating the first low-reliability evaluation area 120 may be set to be larger than the thickness of the mark 400 indicating the second low-reliability evaluation area 120. As another example, a length of the arrow of the mark 400 indicating the first low-reliability evaluation area 120 may be set to be longer than a length of the arrow of the mark 400 indicating the second low-reliability evaluation area 120. As still another example, a color of the mark 400 indicating the first low-reliability evaluation area 120 may be set to red, and a color of the mark 400 indicating the second low-reliability evaluation area 120 may set to green. As described above, as the reliability of the evaluation area 120 is determined to be low, the shape of the mark 400 indicating the evaluation area 120 is differently set, so that the user may more easily recognize the evaluation area 120 in which supplementation is a lot required, and sufficiently supplement and scan the portion of the scan data 300 in which supplementation is a lot required, thereby improving the reliability of the scan data 300.

Meanwhile, the marks 400 displayed to indicate the evaluation area 120 by the indicating operation (S130) may be generated in real time as the scan data 300 is acquired. However, when the marks 400 are generated in real time as the scan data 300 is acquired, an excessive number of the marks 400 are overrun before the supplementation scanning operation is performed, resulting in increasing user confusion. Accordingly, preferably, the marks 400 may be generated and displayed to indicate the evaluation area 120 after the scan data acquiring operation (S110) is completed. In other words, when the scan data acquiring operation (S110) is completed, the reliability determining operation (S120) is performed based on the acquired scan data 300, and the mark 400 for indicating the low-reliability evaluation area 120 determined by the reliability determining operation (S120) may be generated and displayed in the indicating operation (S130). The scan data acquiring operation (S110) may be completed by the user pressuring a specific button of the scan unit 10 (e.g., a handheld three-dimensional scanner). More specifically, the scan data acquiring operation (S110) may be completed by the user pressurizing a scan end/start button.

As described above, since the marks 400 are generated and displayed after the scan data acquiring operation (S110) is completed, it is possible to prevent the marks 400 from being overrun in the initial scan process, and prevent user confusion. In addition, it is possible to prevent unnecessary resource waste of calculating the location, length, direction, etc. of the mark 400 to generate and display the marks 400, and accurately indicate only the portion of the scan data 300 in which supplementation is required.

Hereinafter, a process of changing the general mark 400 to an overlaid mark 500 in the indicating operation (S130) will be described.

Figure 10:
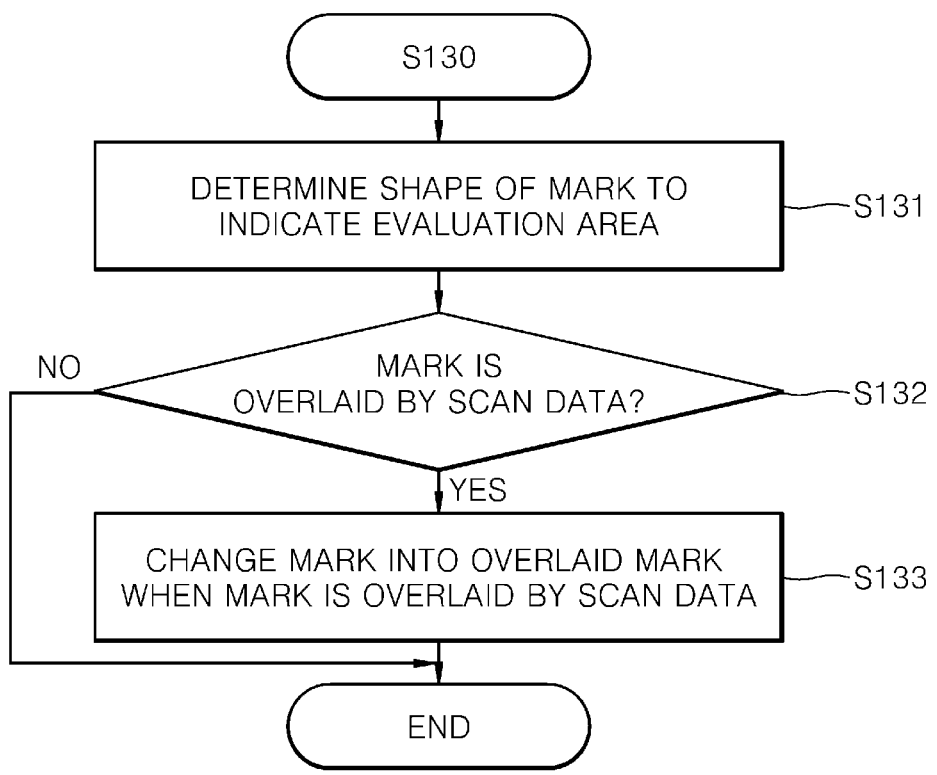
FIG. 10 is an exemplary specific flowchart of an indicating operation (S130) in the data processing method according to the present disclosure.
Figure 11:
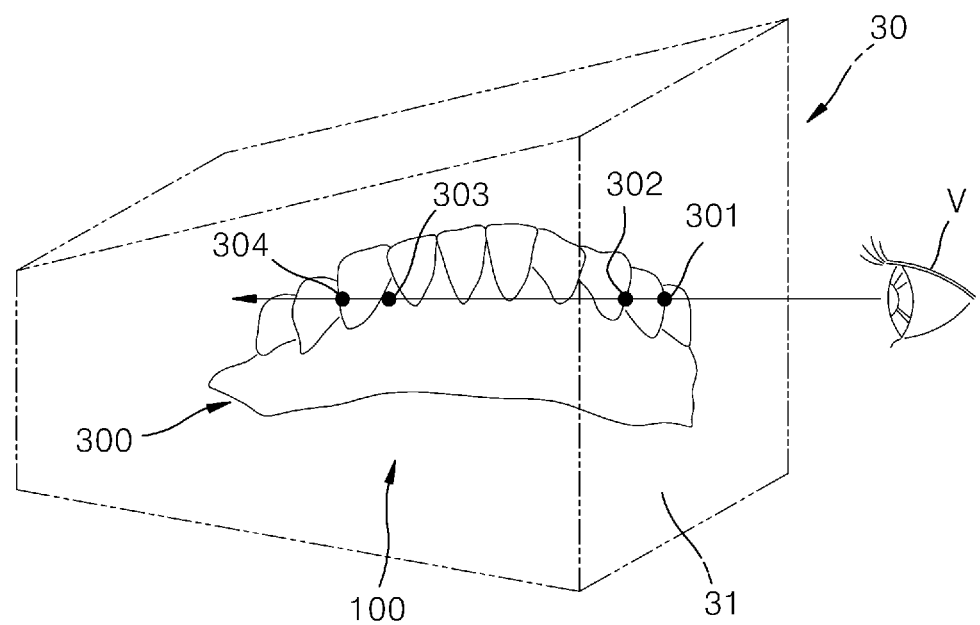
FIG. 11 shows a process of determining whether the mark is overlaid in the data processing method according to the present disclosure.
Figure 12:
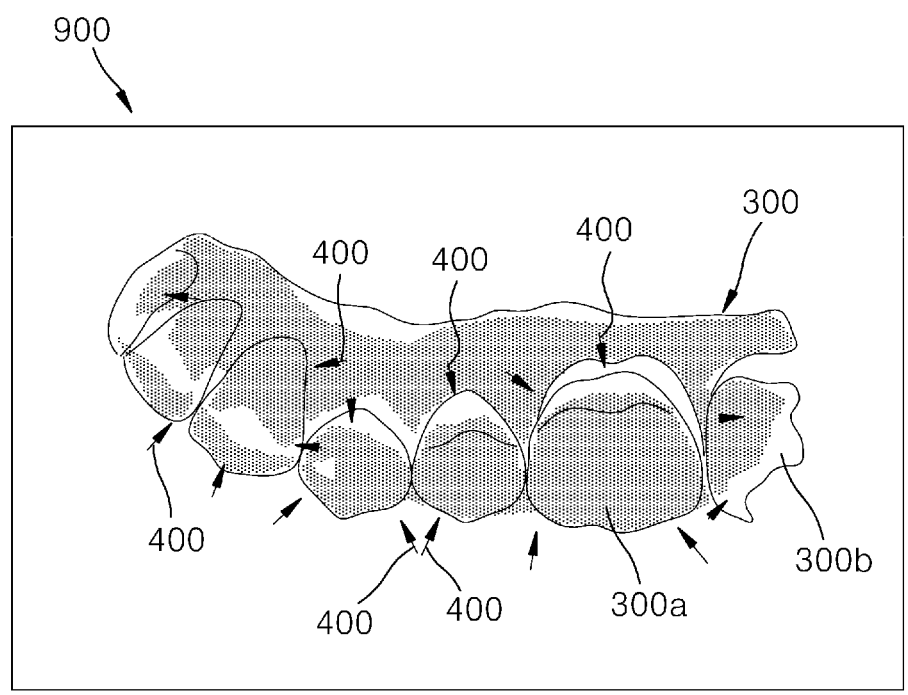
FIG. 12 shows a state in which the mark is displayed when the scan data is displayed in an arbitrary first direction.
Figure 13:
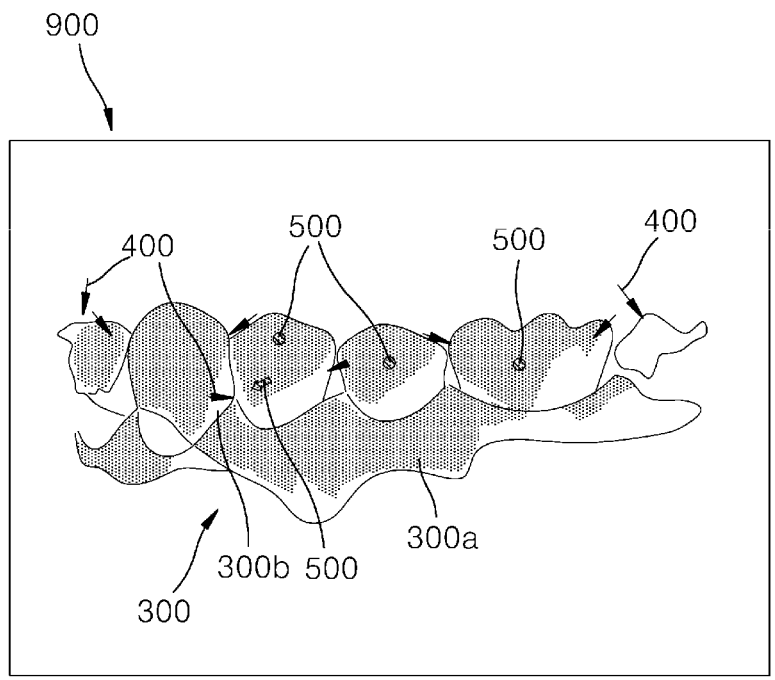
FIG. 13 shows a process of changing some marks into an overlaid mark when the scan data is displayed in an arbitrary second direction.
Figure 14:
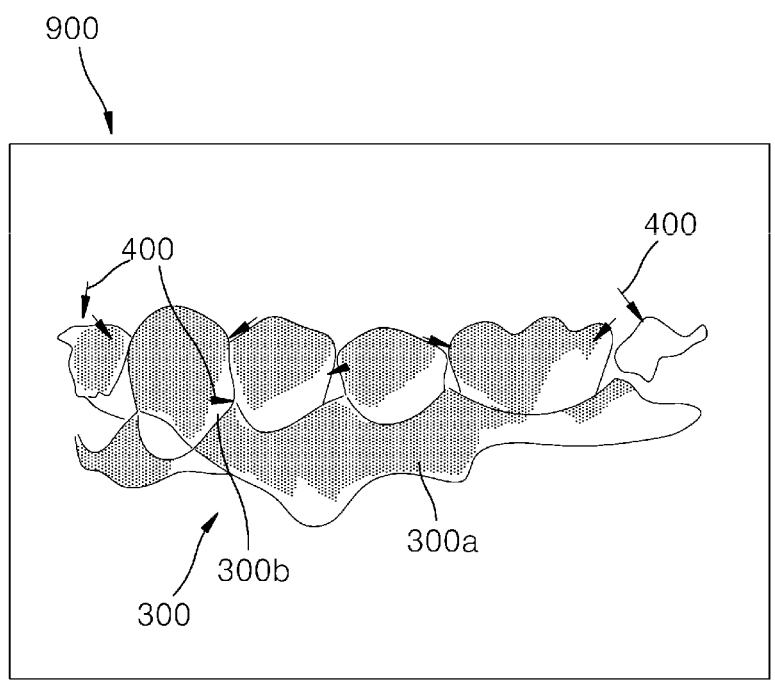
FIG. 14 shows a state in which some marks are overlaid by the scan data and not displayed when the scan data is displayed in the arbitrary second direction.

FIG. 10 is an exemplary specific flowchart of an indicating operation (S130) in the data processing method according to the present disclosure. FIG. 11 shows a process of determining whether the mark 400 is overlaid in the data processing method according to the present disclosure, FIG. 12 shows a state in which the mark 400 is displayed when the scan data 300 is displayed through an arbitrary first direction, FIG. 13 shows a process of changing some marks 400 to the overlaid mark 500 when the scan data 300 is displayed through an arbitrary second direction, and FIG. 14 shows a state in which some marks 400 are overlaid by the scan data 300 and not displayed when the scan data 300 is displayed through an arbitrary second direction.

Referring to FIGS. 10 and 11, the indicating operation (S130) may include a marker shape determining operation (S131), an overlay determining operation (S132), and an overlaid mark determining operation (S133). First, in the mark shape determining operation (S131), the mark management unit may determine the shape of the marker (e.g., at least one of the thickness of the mark, the length of the mark, and the color of the mark) depending on the reliability of the evaluation area 120. Since the process of determining the shape of the mark has been described above, a detailed description thereof will be omitted.

In addition, the mark management unit may determine whether each mark is overlaid by the scan data 300 in the overlay determining operation (S132). As shown in FIG. 11, the scan data 300 may be viewed through a display screen 31 of the display unit 30 by the user's gaze V. At this time, the user may check a surface of the display screen 31 of the scan data 300 existing in the three-dimensional space 100.

In other words, when a virtual light ray by the user's gaze V incident in the normal direction of the display unit 30 on which the scan data 300 is displayed passes through the surface of the scan data n times, it may be determined that a second surface to a nth surface through which the virtual light ray passes have the mark 400 overlaid by the scan data 300 (at this time, n may be 2 or more integer). For example, the virtual light ray generated by the user's gaze V may pass through a first surface 301, a second surface 302, a third surface 303, and a fourth surface 304 of the scan data 300. At this time, the user may substantially see the first surface 301 displayed on the display screen 31, and the second to fourth surfaces 302, 303, 304 are not seen to the user.

When the marks 400 indicated toward the second to fourth surfaces 302, 303, 304 are displayed in the same form as the mark 400 indicated toward the first surface, it may be difficult for the user to accurately identify the portion of the scan data 300 in which supplementation is required. Accordingly, in the overlaid mark determining operation (S133), when the mark 400 is overlaid by the scan data 300, the mark management unit may change the mark 400 to the overlaid mark 500.

As shown in FIG. 12, the scan data 300 is displayed in the arbitrary first direction, and the marks 400 are displayed along with the scan data 300. At this time, since all of the marks 400 indicate the portions on the first surface of the scan data 300, all of the marks 400 shown in FIG. 12 may be general marks.

On the other hand, as shown in FIG. 13, the scan data 300 may be displayed through the arbitrary second direction, and some marks 400 may indicate the nth surface (n is an integer greater than or equal to 2) of the scan data 300 to be overlaid by the scan data 300. Accordingly, the mark 400 overlaid by the scan data 300 may be changed to the overlaid mark 500.

For example, the transparency of the overlaid mark 500 may be higher than that of the general mark 400. There is an advantage in that by setting the transparency of the overlaid mark 500 to be higher than that of the general mark 400, the user may easily check that the evaluation area 120 indicated by the overlaid mark 500 is located on the nth surface (e.g., n is an integer greater than or equal to 2) of the scan data 300, and the user may easily check the shape the first surface of the scan data 300 by the overlaid mark 500.

As shown in FIG. 14, the transparency of the overlaid mark 500 may be 100%. When the transparency of the overlaid mark 500 is 100%, the overlaid mark 500 may not be displayed. As described above, there is an advantage in that when the overlaid mark 500 is transparently processed, only the portion in which supplementation is required may be indicated on the first surface of the scan data 300 by the mark 400, and the user may easily check and supplement the surface on which the scan data 300 is viewed on the display screen 31.

In addition, the overlaid mark 500 may be expressed in a circular shape having a predetermined radius with respect to the center of the evaluation area 120 to indicate the evaluation area. For example, unlike the general mark 400, the overlaid mark 500 may be concisely expressed in a dot shape other than an arrow shape. Accordingly, there is an advantage in that the overlaid mark 500 overlaid by the scan data 300 concisely expresses the location of the portion in which supplementation is required on the nth surface (n is an integer greater than or equal to 2) of the scan data 300 without distortion of the first surface of the scan data 300, thereby improving visibility of the scan data 300 of the user.

The above-described mark 400 may be changed to the overlaid mark 500 by movement, rotation, and tilting of the scan data 300, and the overlaid mark 500 may also be changed to the general mark 400 when indicating the first surface by the movement, rotation, and tilting of the scan data 300.

Meanwhile, as shown in FIGS. 13 and 14, the reliability of the surface of the scan data 300 may also be displayed along with the mark 400 and the overlaid mark 500. For example, the portion of the scan data 300 in which the evaluation area 120 is the high-reliability evaluation area 120 may be displayed as a first pattern 300*a*, and the portion of the scan data 300 in which the evaluation area 120 is the low-reliability evaluation area 120 may be displayed as a second pattern 300*b*. The first pattern 300*a* may be green and the second pattern 300*b* may be red, but they are not necessarily limited to the listed examples. As described above, there is an advantage in that since the reliability of the surface of the scan data 300 is displayed along with the mark 400 and the overlaid mark 500, the user may more easily check the portion of the scan data 300 in which supplementation is required, and quickly supplement the scan data 300, thereby improving the reliability of the scan data 300.

Hereinafter, a process of supplementing the scan data 300 marked with the mark 400 by the low-reliability evaluation area 120 will be described.

Figure 15:
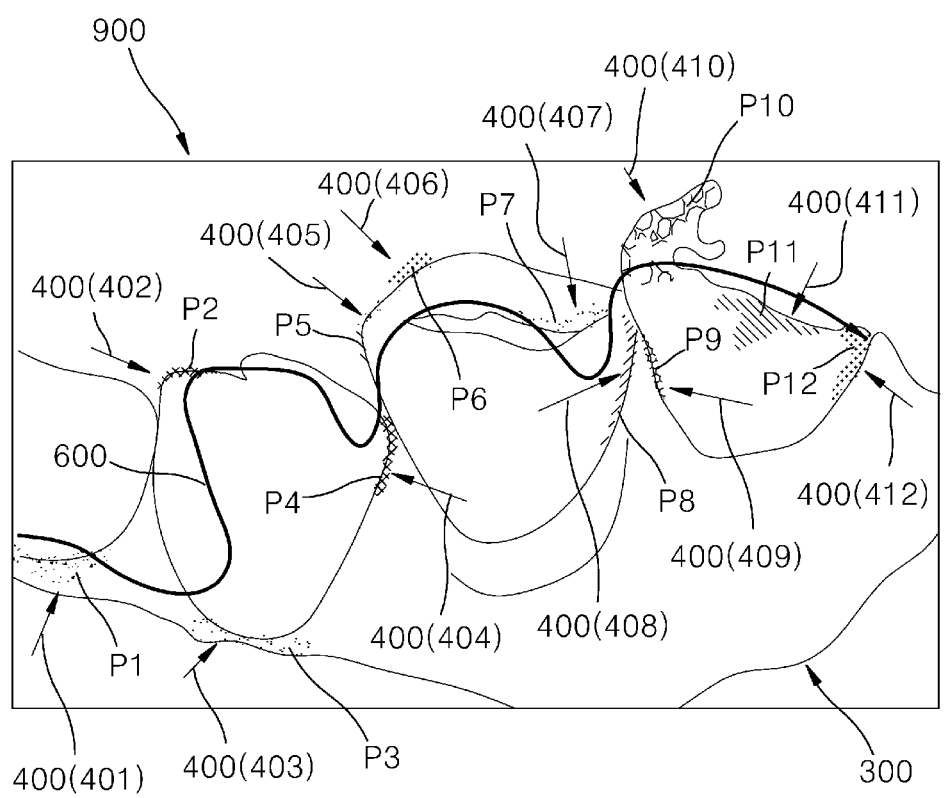
FIG. 15 shows a supplementation scan operation in the data processing method according to the present disclosure.

FIG. 15 shows the supplementation scanning operation (S140) in the data processing method according to the present disclosure.

Referring to FIGS. 2 and 15, the data processing method according to the present disclosure may further include a supplementation scanning operation (S140). In the supplementation scanning operation (S140), the user may acquire additional supplementation scan data for supplementing the scan data 300 acquired in the scan data acquiring operation (S110) using the scan unit. At this time, the user may pressurize the scan end/start button to perform the supplementation scanning operation (S140). When the supplementation scanning operation (S140) is performed, the mark 400 and/or the overlaid mark 500 generated by the indicating operation (S130) are not removed even when the supplementation scanning operation (S140) is started, and the user may additionally scan the object along a supplementation scan path 600. In particular, in the supplementation scan operation (S140), the user may acquire supplementation scan data in consideration of the portion and direction indicated by the mark 400 or the overlaid mark 500 using the scan unit.

Figure 16:
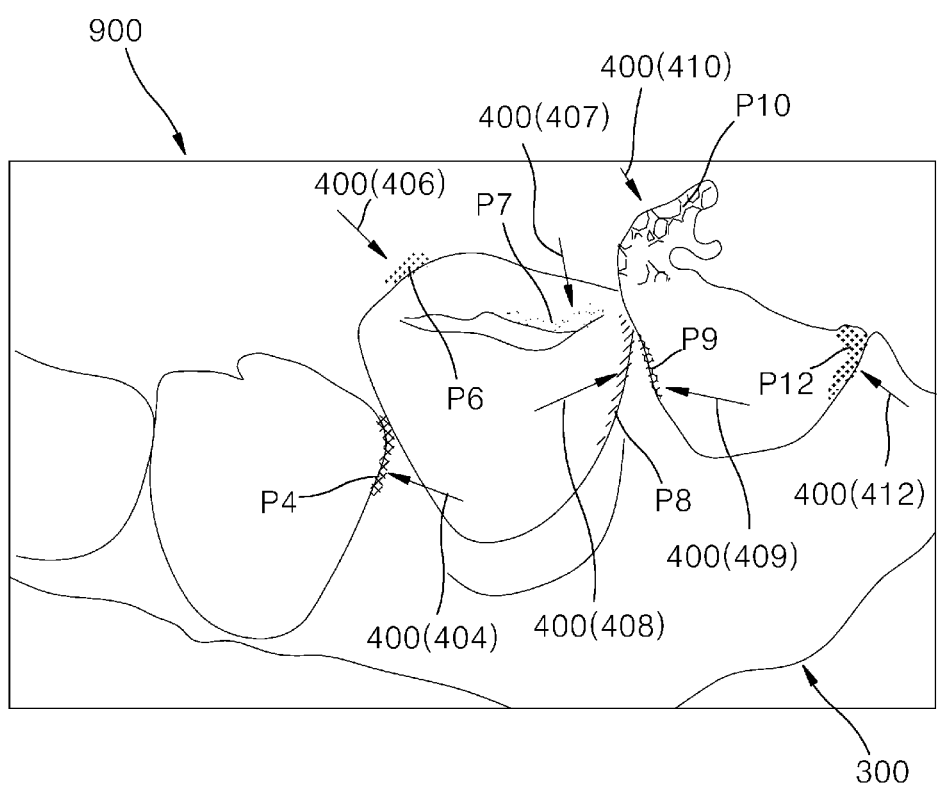
FIG. 16 shows a mark updating operation in which some marks are removed as the supplementation scan operation is performed in the data processing method according to the present disclosure.

FIG. 16 shows a mark updating operation (S150) with some marks removed as the supplementation scan operation (S140) is performed in the data processing method according to the present disclosure.

Referring to FIGS. 2 and 16, the data processing method according to the present disclosure may further include the mark updating operation (S150). In the supplementation scan operation (S140), when the user acquires additional supplementation scan data, the reliability of the evaluation area 120 may be updated by the supplementation scan data acquired in the supplementation scanning operation (S140). For example, in the low-reliability evaluation area 120, the number of three-dimensional points 200 of the unit areas 120 included in the low-reliability evaluation area 120 increases or the scan angle range increases, so that the reliability of the corresponding evaluation area 120 may be updated, and the corresponding evaluation area 120 may be converted into the high-reliability evaluation area 120. Accordingly, in the mark updating operation (S150), the mark management unit may remove the mark 400 or the overlaid mark 500 indicating the evaluation area 120 converted into the high-reliability evaluation area 120 in real time. As exemplarily shown in FIG. 16, a first mark 401, a second mark 402, a third mark 403, a fifth mark 405, and an eleventh mark 411 are removed by the increase in reliability by the acquisition of the supplementation scan data. The mark 400 or the overlaid mark 500 is removed in real time by the acquisition of the additional supplementation scan data, so that the user may check visually and easily the process of supplementing the scan data 300, and the user may quickly and efficiently improve the reliability of the scan data 300. As a result, there are advantages in that the user may design and provide an accurate orthodontic treatment product to the patient by effectively supplementing the scan data 300, and provide the optimal treatment to the patient.

The above description is merely illustrative of the technical spirit of the present disclosure, and various modifications and changes will be possible by those skilled in the art to which the present disclosure pertains without departing from the essential characteristics of the present disclosure.

Accordingly, the embodiments disclosed in the present disclosure are not intended to limit the technical spirit of the present disclosure but to describe the same, and the scope of the technical spirit of the present disclosure is not limited by these embodiments. The scope of the present disclosure should be interpreted by the appended claims, and all technical spirits within the scope equivalent thereto should be interpreted as being included in the scope of the present disclosure.

The invention claimed is:

1. A data processing method comprising:
a scan data acquiring operation of acquiring scan data expressing an object by a scanner;
a reliability determining operation of determining a reliability of at least one evaluation area including at least one unit area for evaluating the scan data; and
an indicating operation of indicating the evaluation area as a predetermined mark depending on the reliability of the evaluation area by a display,
wherein a plurality of unit areas are included in the evaluation area, and
the reliability of the evaluation area is determined at a ratio of the unit area satisfying a predetermined condition within the evaluation area.

2. The method of claim 1,
wherein the evaluation area is partitioned and generated in a three-dimensional space to correspond to the scan data after the scan data is acquired.

3. The method of claim 1,
wherein the evaluation area is previously partitioned and generated in a three-dimensional space before the scan data is acquired.

4. The method of claim 1,
wherein a shape of the mark includes: a three-dimensional arrow directed to a center of the evaluation area.

5. The method of claim 4,
wherein a direction of the mark is parallel to a direction of an average normal vector of three-dimensional points included in the evaluation area.

6. The method of claim 4,
wherein the mark has a different shape depending on the reliability of the evaluation area.

7. The method of claim 6,
wherein as the reliability of the evaluation area is determined to be low, a length of the mark indicating the evaluation area is set to be long.

8. The method of claim 1,
wherein the scan data includes: a tooth area expressing a tooth of the object, and a gum area expressing a gum of the object, and
the reliability determining operation is performed on at least a part of the tooth area.

9. The method of claim 8,
wherein the reliability determining operation is also performed on at least a part of the gum area.

10. The method of claim 1,
wherein the mark is displayed to indicate the evaluation area after the acquisition of the scan data is completed.

11. The method of claim 1, further comprising: a supplementation scanning operation of acquiring additional supplementation scan data for supplementing the scan data acquired in the scan data acquiring operation,
wherein the mark is removed in real time as the reliability of the evaluation area is updated by the supplementation scan data acquired in the supplementation scanning operation.

12. The method of claim 1,
wherein the indicating operation includes:
a mark shape determining operation of determining a shape of the mark to indicate the evaluation area;
an overlay determining operation of determining whether the mark is overlaid by the scan data; and
an overlaid mark determining operation of changing the mark into an overlaid mark when the mark is overlaid by the scan data.

13. The method of claim 12,
wherein transparency of the overlaid mark is higher than transparency of the mark.

14. The method of claim 12,
wherein the overlaid mark is expressed as a circular shape having a predetermined radius with respect to a center of the evaluation area to indicate the evaluation area.

15. The method of claim 12,
wherein when a virtual light ray incident in a normal direction of the display on which the scan data is displayed passes through a surface of the scan data n times, the overlay determining operation determines that the marks on a second surface to a nth surface through which the virtual light ray passes are overlaid by the scan data (n is an integer greater than or equal to 2).

16. A data processing method comprising:
a scan data acquiring operation of acquiring scan data expressing an object by a scanner;
a reliability determining operation of determining a reliability of at least one evaluation area including at least one unit area for evaluating the scan data; and
an indicating operation of indicating the evaluation area as a predetermined mark depending on the reliability of the evaluation area by a display,
wherein the unit area has a form of voxel data, and
the reliability of the evaluation area is determined by comparing the number of three-dimensional points of the voxel data with the number of threshold points.

17. A data processing method comprising:
a scan data acquiring operation of acquiring scan data expressing an object by a scanner;
a reliability determining operation of determining a reliability of at least one evaluation area including at least one unit area for evaluating the scan data; and
an indicating operation of indicating the evaluation area as a predetermined mark depending on the reliability of the evaluation area by a display,
wherein the unit area has a form of voxel data, and
the reliability of the evaluation area is determined by comparing a scan angle range of the three-dimensional point of the voxel data with a threshold scan angle range.

* * * * *